(12) United States Patent
Short

(10) Patent No.: US 6,356,940 B1
(45) Date of Patent: Mar. 12, 2002

(54) METHOD AND SYSTEM OF ELECTRONICALLY LOGGING REMOTE USER DIETARY INFORMATION, AND GENERATING AND AUTOMATICALLY SENDING SUGGESTED DIETARY MODIFICATIONS

(76) Inventor: Brian Robert Short, 1612 Duvall Dr., San Jose, CA (US) 95130

( * ) Notice: Subject to any disclaimer, the term of this patent is extended or adjusted under 35 U.S.C. 154(b) by 0 days.

(21) Appl. No.: 09/320,037

(22) Filed: May 26, 1999

(51) Int. Cl.[7] .......................... G06F 15/16; G06F 17/30
(52) U.S. Cl. ........................ 709/217; 709/203; 709/229; 707/3
(58) Field of Search ............................. 709/203, 217, 709/229; 705/2, 10; 707/3

(56) References Cited

U.S. PATENT DOCUMENTS

| | | | | |
|---|---|---|---|---|
| 5,749,081 A | * | 5/1998 | Whiteis | 707/102 |
| 5,884,282 A | * | 3/1999 | Robinson | 705/27 |
| 5,909,023 A | * | 6/1999 | Ono et al. | 235/380 |
| 5,918,014 A | * | 6/1999 | Robinson | 706/12 |
| 6,006,264 A | * | 12/1999 | Colby et al. | 709/226 |
| 6,092,049 A | * | 7/2000 | Chislenko et al. | 705/10 |
| 6,159,131 A | * | 12/2000 | Pfeffer | 482/8 |
| 6,189,033 B1 | * | 2/2001 | Jin et al. | 709/225 |
| 6,263,330 B1 | * | 7/2001 | Bessette | 707/4 |

* cited by examiner

Primary Examiner—Krisna Lim
(74) Attorney, Agent, or Firm—Brian R. Short (57) ABSTRACT

A nutritional planning system comprising a plurality of databases such as: a nutrition, a user diet, a recommended diet databases and at least two programs: a nutritional analysis program and a nutritional suggestion program. This nutritional planning system is operational on a host server connected to a computer network for providing communication between the host server and a plurality of remote individual users. The nutrition planning system, further, performs the following step: a) receiving dietary information over a computer network from remote user; b) analyzing the nutritional composition of the dietary information; c) generating suggested modification to the remote user's diet; d) generating suggested modifications to the remote user's diet; e) providing products information which can be used to improve the remote users dietary intake; and f) automatically notifying the remote user over the electronic network of the suggested modification and remote information.

14 Claims, 7 Drawing Sheets

DISPLAY THE MANUFACTURER LIST GENERATED BY THE MANUFACTURER SUGGESTION PROGRAM TO THE REMOTE USER

710

RECEIVE ANY REQUEST BY THE REMOTE USERS TO PURCHASE A MANUFACTURER PRODUCT ON THE MANUFACTURER LIST

720

PROCESS THE MANUFACTURER PRODUCT REQUEST OF THE REMOTE USERS

METHOD AND SYSTEM OF ELECTRONICALLY LOGGING REMOTE USER DIETARY INFORMATION, AND GENERATING AND AUTOMATICALLY SENDING SUGGESTED DIETARY MODIFICATIONS

FIELD OF INVENTION

This invention relates generally to a method and system for electronically receiving and processing dietary information from individuals. More particularly, this invention relates to a method and system for receiving dietary information over an electronic network from remote users, analyzing the nutritional composition of the dietary information, generating suggested modifications to the remote user's diet, providing products information which can be used to improve the remote users dietary intake, and automatically notifying the remote users over the electronic network of the suggested modifications and product information.

BACKGROUND

A method of improving an individual's health includes monitoring the nutritional intake of the individual, and the implementing corrective steps to compensate for excesses and deficiencies in the individual's nutritional intake.

Monitoring an individual's nutritional intake can be difficult. The food consumed by the individual must by recorded or logged. Logging an individual's food consumption can be difficult because of the inconvenience and hassle of logging all the food the individual has consumed. Additionally, the individual may forget exactly what food he or she has consumed before having a chance to log the food. The individual may be traveling or have a job which makes it difficult to log the food the individual consumed.

Once the food consumption of an individual has been recorded, the nutritional content of the food consumed must be calculated. Calculation of the nutritional content requires estimating the nutritional content of each individual piece of food, and summing the nutritional contents of all consumed food. Estimating the nutritional content of individual types of food can be time consuming and laborious. Generally, the nutritional components (calories, vitamins, minerals, fat, protein, carbohydrates) of each food type must be obtained from a table which lists the nutritional components. The nutritional components for all the food types must be recorded, and summed to determine the dietary consumption of the individual. Typically, the individual effort required to calculate the nutritional content of the food consumed is great enough to discourage the individual from completing the calculation.

Correcting excesses and deficiencies in the individual's dietary intake can also be difficult. After calculating the dietary intake of the individual, the calculated dietary intake must be compared with a recommended dietary intake to determine the differences between the actual and recommended dietary intakes. Generally, the actual intake will include too much of some nutritional components (for example fat and calories) and too little of other nutritional component (for example calcium and protein).

Excesses in the individual's dietary intake can be corrected by reducing the consumption of food which provide the excess nutritional components. However, new food types must generally be introduced to the individual's diet to eliminate deficiencies. It can be difficult for the individual to identify food types which provide the nutritional components that the individual's diet is deficient.

It is desirable to have a nutritional planning system for conveniently receiving dietary information from individuals. The nutritional planning system should analyze the nutritional composition of the dietary information and generate suggested modifications to the remote user's diet. The nutritional planning system should suggest products which can be used to improve the individual's dietary intake. Finally, the nutritional planning system should automatically notify the individuals of the suggested modifications and product information.

SUMMARY OF THE INVENTION

The present invention includes a dietary planning method and system for receiving dietary information over an electronic network from remote users, analyzing t he nutritional composition of the dietary information, generating suggested modifications to the remote user's diet, providing products information which can be used to improve the remote users dietary intake, and automatically notifying the remote users over the electronic network of the suggested modifications and product information. Additionally, the suggested products can be electronically ordered by the remote users. The invention can be used by health food companies, vitamin companies and diet supplement companies to help them reach potential customers. Once customers have been reached, the invention provides an easy method for the customers to purchase products offered by the companies.

A first embodiment of this invention includes a nutritional planning system operational on a host server connected to a computer network. The computer network provides communication between the host server and a plurality of remote individual users. The nutritional planning system includes a nutrition database, a user diet database, a recommended diet database, a nutritional analysis program and a nutritional suggestion program. The nutrition database is in communication with the host server. The nutrition database includes dietary components of a plurality of food types. The user diet database is in communication with the remote users and in communication with the host server. The user diet database receives dietary information from the remote users. The dietary information includes foods consumed by the remote users. The recommended diet database is in communication with the host server. The recommended diet database includes recommended dietary information. The nutritional analysis program and the nutritional suggestion program are operational on the host server. The nutritional analysis program determines the nutritional composition of the dietary information of the remote users by retrieving the dietary components of food types within the nutrition database which corresponds with the foods consumed by the remote users. The nutritional composition of the dietary information of the remote user is automatically communicated through the computer network to each of the remote users. The nutritional suggestion program generates suggested modifications of the remote user's diet to improve the dietary composition of each remote user's diet based upon the dietary information of the remote user and the recommended dietary information stored within the recommended diet database. The suggested modifications of the remote user's diet is automatically communicated through the computer network to the remote users.

A second embodiment is similar to the first embodiment. The second embodiment further includes a product suggestion database an d a product suggestion program. The product suggestion database is in communication with the host server. The product suggestion database includes products which can be suggested to each remote user based upon the suggested modifications of the remote users diet. The product suggestion program generates a product list that includes products within the product suggestion database which can be consumed by individual remote users to improve the dietary consumption of the remote users. The product list is automatically communicated through the computer network to the remote users.

A third embodiment is similar to the second embodiment. The third embodiment further includes a manufacturer database and a manufacturer suggestion program. The manufacturer database is in communication with the host server. The manufacturer database includes manufacturer products which are substantially similar to the products of the product list. The manufacturer suggestion program generates a manufacturer list including manufacturer products within the manufacturer database which can be consumed by individual remote users to improve the dietary consumption of the remote users. The manufacturer list is automatically communicated through the computer network to the remote users.

A fourth embodiment is similar to the third embodiment. The fourth embodiment further includes a manufacturer transaction program. The manufacturer transaction program receives money orders from remote users for manufacturer products, sends the orders to a corresponding manufacturer, and automatically sends an acknowledgment of the order to the remote user who initiated the money order.

Other aspects and advantages of the present invention will become apparent from the following detailed description, taken in conjunction with the accompanying drawings, illustrating by way of example the principles of the invention.

DETAILED DESCRIPTION

As shown in the drawings for purposes of illustration, the invention is embodied in a method and system for receiving dietary information over an electronic network from remote users, analyzing the nutritional composition of the dietary information, generating suggested modifications to the remote user's diet, providing products information which can be used to improve the remote users dietary intake, and automatically notifying the remote users over the electronic network of the suggested modifications and product information.

Figure 1:
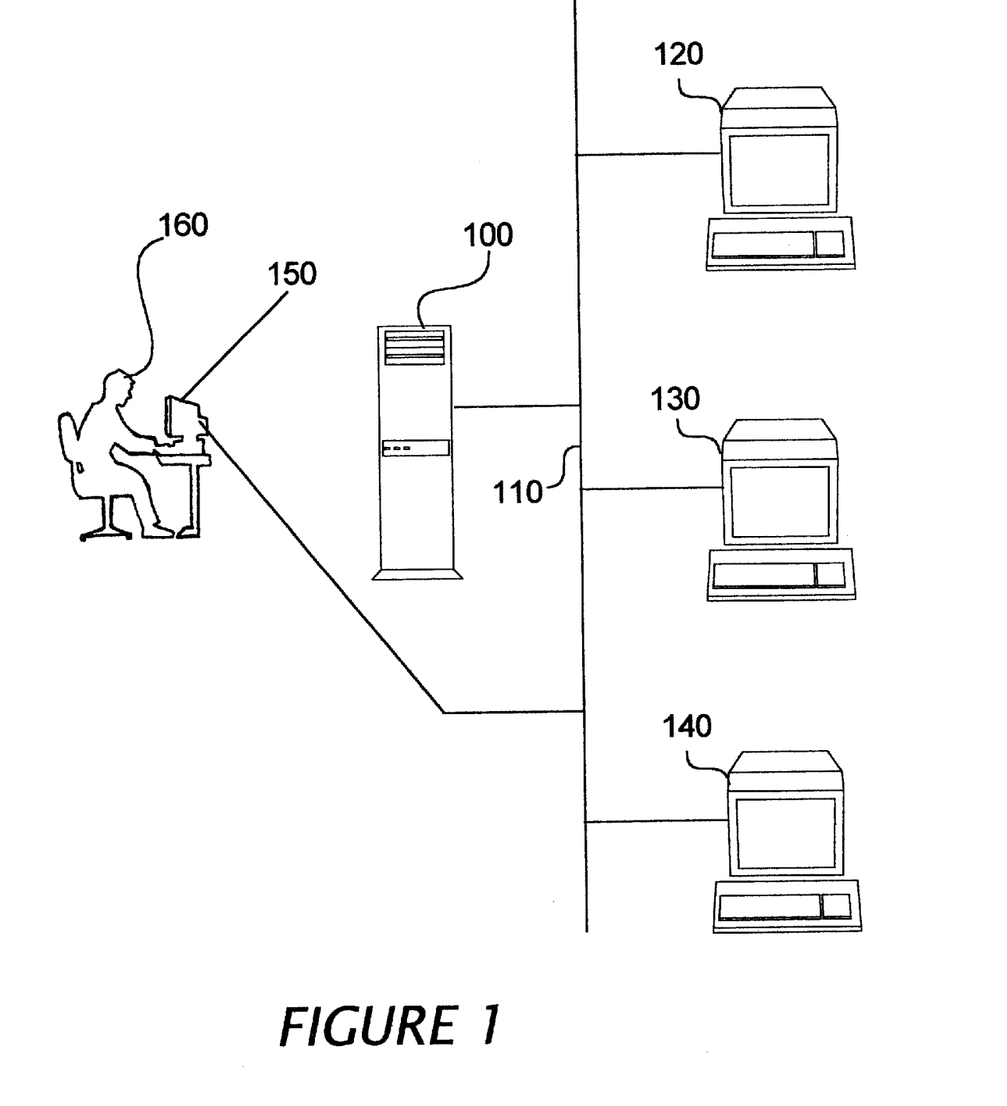
FIG. 1 shows a computer networking system which can be used to implement the system and method of the invention.

FIG. 1 shows a computer networking system which can be used to implement the system and method of the invention.

The computer networking system includes a host server 100 connected to a network 110 and several remote user terminals 120, 130, 140. A host server administrator 150 can enter control parameters and commands directly to the host server 100. FIG. 1 only shows a single host server administrator 150. However, the invention can include more than one host server administrator 150. The host server administrator 150 is distinguished from the remote users in that the host server administrator 150 has greater priority in accessing and modifying information within the databases of the computer networking system.

The remote user terminals 120, 130, 140 allow remote users to access computer programs and databases which are controlled by the host server 100 through the network 110. The host server 100 can provide access to information within the databases through a web page which the remote users can access through the network 110. The web page is controlled by the host server 100, and generates a screen view for display to the remote users. During a remote user's web page access, the web page provides menu selections of programs and information relevant to the purposes of the web page. Upon the remote user selection of a menu item, the host server 100 displays on the web page corresponding program information or up-to-date information.

Figure 2:
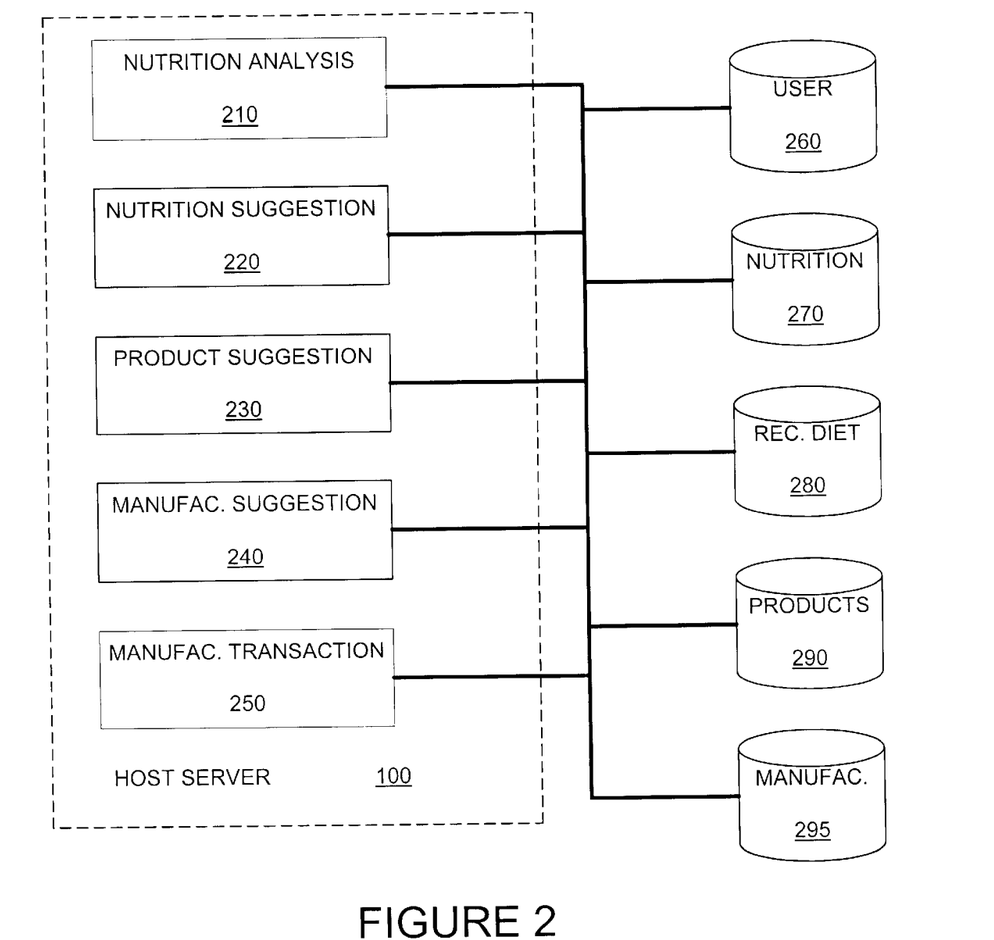
FIG. 2 shows an embodiment of the invention which includes the host server, computer programs according to the invention which run on the host server, and several databases which are accessed by the remote users, network administrators and the host server.

FIG. 2 shows an embodiment of the invention which includes the host server 100, computer programs 210, 220, 230, 240, 250 according to the invention which run on the host server 100, and various databases 260, 270, 280, 290, 295 which can be accessed by the remote users and the host server 100.

The computer programs of the invention include a nutritional analysis program 210, a nutrition suggestion program 220, a product suggestion program 230, a manufacturer suggestion program 240, and a manufacturer transaction program 250. The databases of the invention include a user diet database 260, a nutrition database 270, a recommended diet database 280, a product suggestion database 290, and a manufacturer database 295.

The nutritional analysis program 210 determines the nutritional composition of the dietary information of the remote users by retrieving the dietary components of food types within the nutrition database 270 which correspond with the foods consumed by the remote users.

The nutritional suggestion program 220 generates suggested modifications of the remote user's diet to improve the dietary composition of each remote user's diet based upon the dietary information of the remote user and recommended dietary information stored within the recommended diet database 280.

The product suggestion program 230 generates a product list including products within the product suggestion database 290 which can be consumed by individual remote users to improve the dietary consumption of the remote users.

The manufacturer suggestion program 240 generates a manufacturer list including manufacturer products within the manufacturer database which can be consumed by individual remote users to improve the dietary consumption of the remote users.

The manufacturer transaction program 250 receives money orders from remote users for manufacturer products, sends the orders to a corresponding manufacturer, and automatically sends an acknowledgment of the order to the remote user who initiated the money order.

The user diet database 260 is in communication with the remote users and in communication with the host server. The user diet database 260 receives dietary information from the remote users. The dietary information includes foods consumed by the remote users. Generally, both the remote users and the host server administrator 150 can modify the information stored within the user diet database 260.

The nutrition database 270 is in communication with the host server 100. The nutrition database 270 includes dietary components of a plurality of food types. Generally, only the host server administrator 150 can modify the information stored within the nutrition database 270.

The recommended diet database 280 is in communication with the host server 100. The recommended diet database 280 includes recommended dietary information. Generally, only the host server administrator 150 can modify the information stored within the recommended diet database 280.

The product suggestion database 290 is in communication with the host server. The product suggestion database 290 includes products which can be suggested to each remote user based upon the suggested modifications of the remote users diet. Generally, only the host server administrator 150 can modify the information stored within the product suggestion database 290

The manufacturer database 295 is in communication with the host server. The manufacturer database 295 includes manufacturer products which are substantially similar to the products of the product list. Generally, only the host server administrator 150 can modify the information stored within the manufacturer database 295.

A first aspect of the invention includes a nutritional planning computer system and method which allows many individuals to electronically log dietary information including foods consumed by the individuals, and automatically receive the nutritional composition of the dietary information. The electronic logging process primarily involves the nutritional analysis program 210, the user diet database 260 and the nutrition database 270.

The host server 100 receives dietary information of remote users which is to be logged, through the network 110. Typically, the dietary information is input to the host server 1 00 through a web page associated with the nutritional planning system.

The host server 100 provides instructions about how personal information and foods consumed by the remote users are to be entered. The information input by the remote user is generally stored in the user diet database 260. Typically, this information can include the remote user's age, gender, weight, height, level of physical activity, and most importantly, the foods consumed by the remote user. Additionally, the information can also include a form of payment, like, a credit card number. The foods consumed by the remote user can be entered (logged) on a multi-daily, daily, or sub-daily bases. The foods consumed includes anything orally consumed by the remote user. This includes foods from the basic food group, supplements and vitamins.

The host server 100 then causes the nutritional analysis program 210 to be executed. The nutritional analysis program 210 can be executed on a multi-daily, daily, or sub-daily bases. The more frequently the nutritional analysis program 210 is executed, the sooner dietary corrections can be implemented into the remote user's diet.

Figure 3:
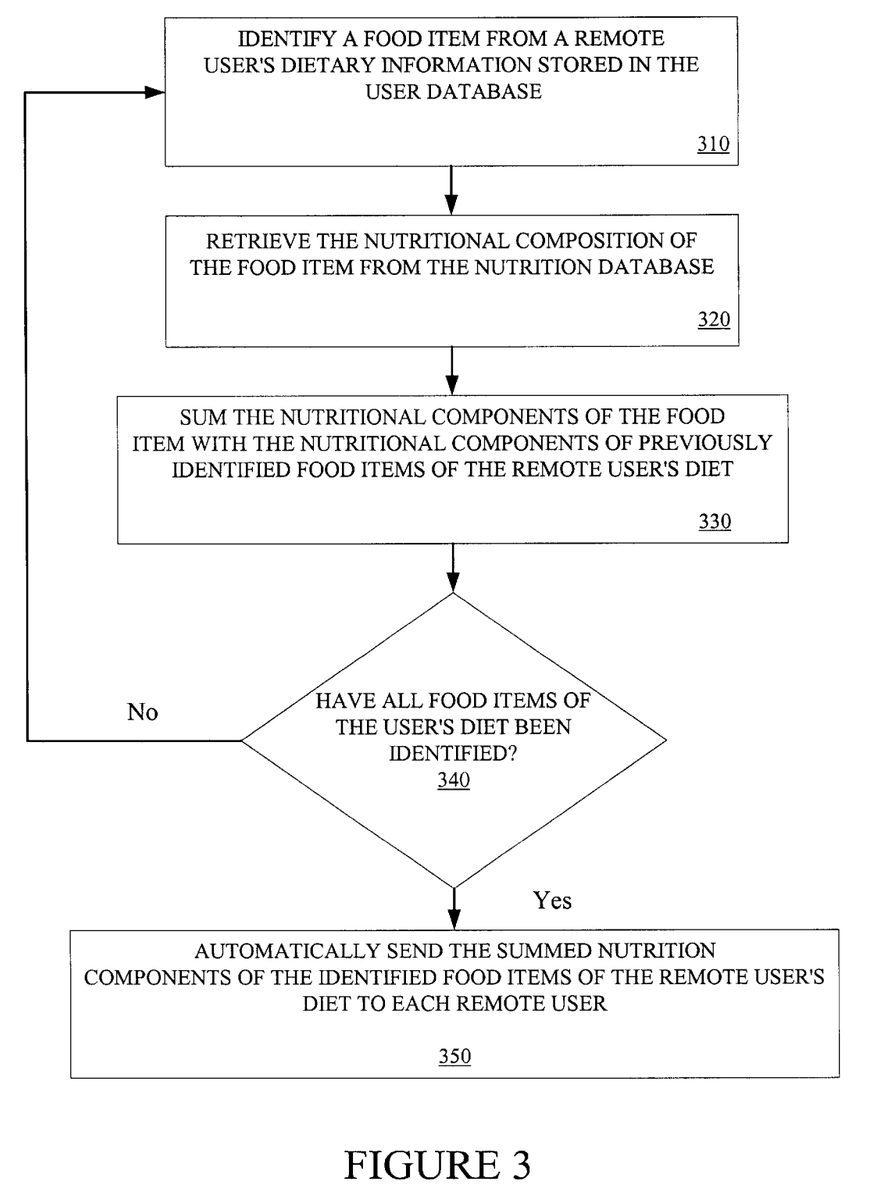
FIG. 3 is a flow chart which shows the steps included within a nutritional analysis program.

FIG. 3 shows a flow chart of the steps included within the nutritional analysis program 210 according to the invention. As previously stated, the nutritional analysis program 210 determines the nutritional composition of the dietary information of the remote users by retrieving the dietary components of food types within the nutrition database 270 which correspond with the foods consumed by the remote users.

A first step 310 includes identifying a food item from a remote user's dietary information stored in the user diet database 260. Generally, the dietary information of the remote user will include a plurality of food items. The first step includes identifying a single food item which is to be analyzed individually.

A second step 320 includes retrieving the nutritional composition of the food item from the nutrition database 270. The nutritional composition can include calories, vitamins, minerals, protein, carbohydrates and fat of the food item. Other nutritional components of the food items can also be included within the nutrition database 270.

A third step 330 includes summing the nutritional components of the food item with the corresponding nutritional components of previously identified food items of the remote user's diet.

A fourth step 340 includes determining whether all food items of the user's diet been identified and summed with the other food items of the user's diet. If at least one food item has not been identified and summed, then first step 310 is repeated. If all of the food item(s) have been identified and summed, the a fifth step 350 is executed.

The fifth step 350 includes electronically communicating the summed nutrition components of the identified food items of the remote user's diet to each remote user. The communication can be in the form of an electronic mail message sent to the remote user. The electronic mail can be sent to an electronic mail address stored in the user diet database at the time the remote user inputs personal information. Alternatively, the communication can be in the form of storing the summed nutrition components of the identified food items of the remote user's diet in a database which is accessible by the remote user through, for example, the web page associated with the nutritional planning system.

Figure 4:
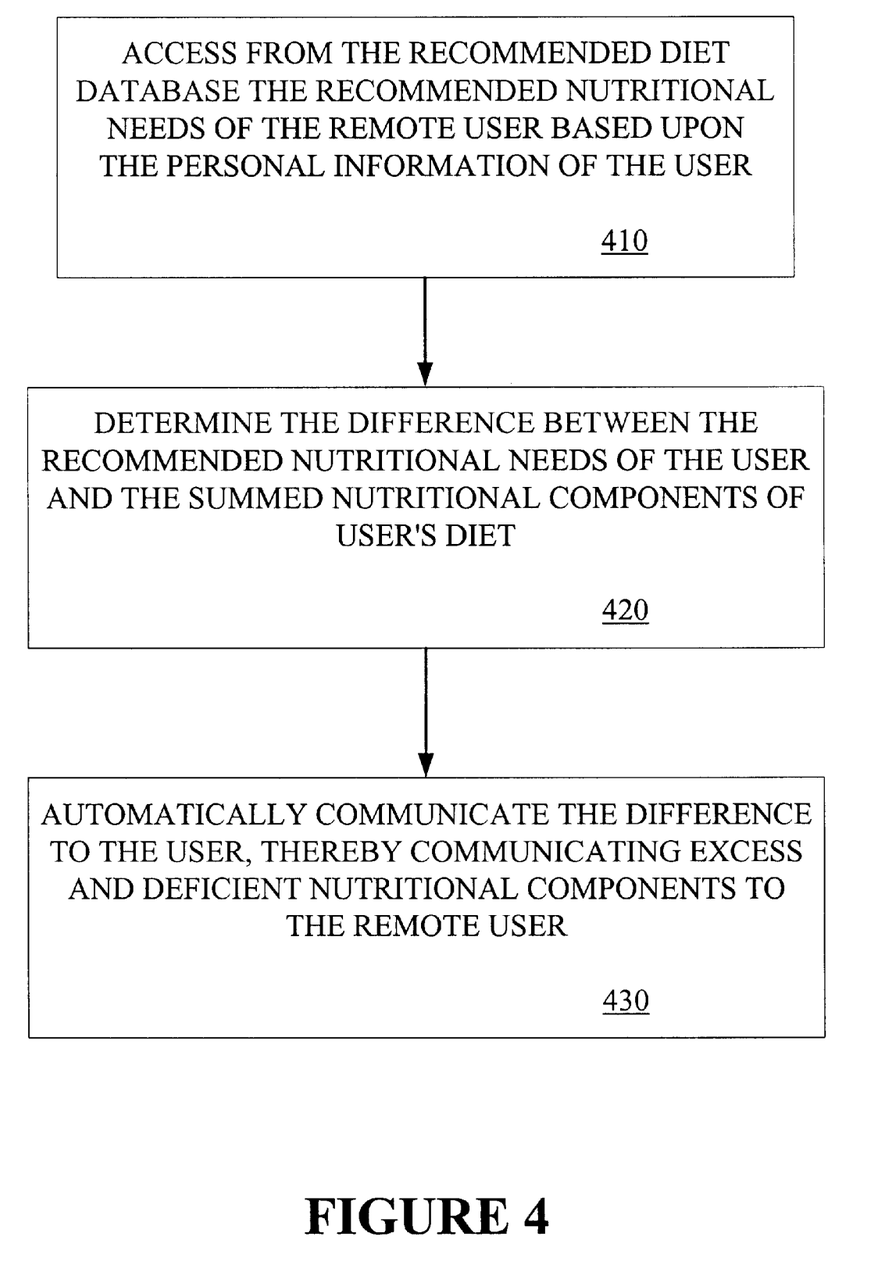
FIG. 4 is a flow chart which shows the steps included within a nutrition suggestion program.

Another aspect of the invention includes electronically generating suggested modifications of the remote user's diet to improve the dietary composition of each remote user's diet based upon the dietary information of the remote user and the recommended dietary information stored within the recommended diet database 280, and automatically communicating the suggested modifications of the remote user's diet to the remote users.

FIG. 4 is a flow chart which shows the steps included within the nutritional suggestion program 220. As previously stated, the nutritional suggestion program 220 generates suggested modifications of the remote user's diet to improve the dietary composition of each remote user's diet based upon the dietary information of the remote user and recommended dietary information stored within the recommended diet database 280. The recommended dietary information can be based on one of several sources.

A first step 410 includes accessing the recommended nutritional needs of the remote user based upon personal information of the user, from the recommended diet database 280. The recommended nutritional needs of the individual can be based on one or more sources. For example, the recommended nutritional needs can be based on information published by the Federal government. Alternatively, the recommended nutritional needs can be based upon information published by a private organization or company. The recommended nutritional needs can be based on whether the individual desires to obtain muscle mass, lose weight, gain weight, increase body defenses or reduce body fat. The remote user's primary goals can be included within the recommended nutritional needs of the remote user.

A second step 420 includes determining the difference between the recommended nutritional needs of the user and the summed nutritional components of the user's diet.

A third step 430 includes automatically communicating the difference to the user, thereby communicating excess and deficient nutritional components to the remote user. The communication can be in the form of an electronic mail message sent to the remote user. The electronic mail can be sent to an electronic mail address stored in the user diet database at the time the remote user inputs personal information. Alternatively, the communication can be in the form of storing the difference a database which is accessible by the remote user through, for example, the web page associated with the nutritional planning system.

Figure 5:
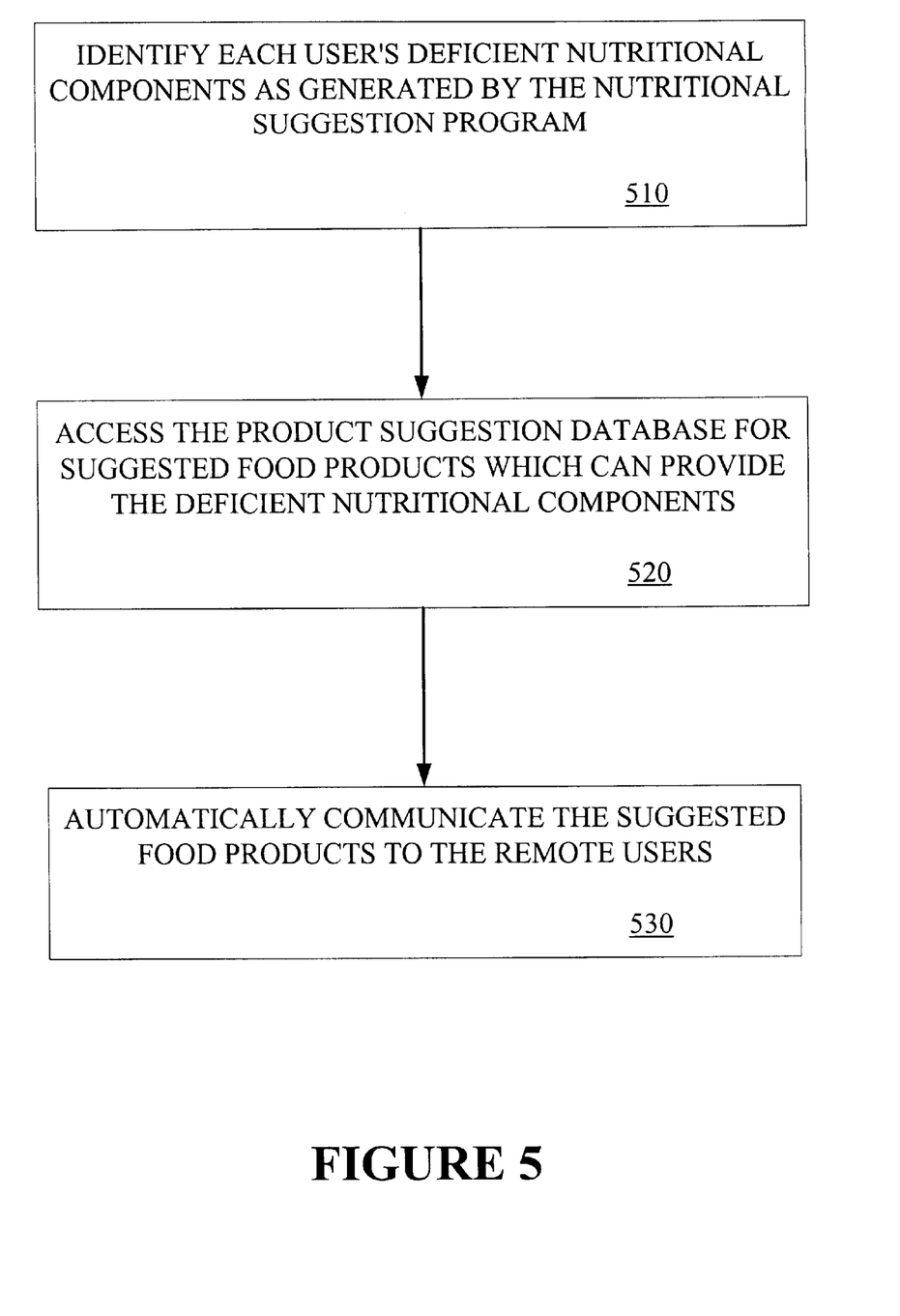
FIG. 5 is a flow chart which shows the steps included within a product suggestion program.

Another aspect of the invention includes electronically generating a product list which includes products within the product suggestion database 290 which can be consumed by individual remote users to improve the dietary consumption of the remote users, and automatically communicating the product list to the remote users. The products lists includes food items such as types of meats (such as chicken, beef or turkey), vegetables (such as corn, carrots or beets), or dairy products (such as milk, cheese or yogurt). Additionally, the product list can include vitamins and minerals.

FIG. 5 is a flow chart which shows the steps included within a product suggestion program 230. As previously stated, the product suggestion program 230 generates a product list including products within the product suggestion database 290 which can be consumed by individual remote users to improve the dietary consumption of the remote users.

A first step 510 includes identifying each user's deficient nutritional components as generated by the nutritional suggestion program 220.

A second step 520 includes accessing the product suggestion database 290 for suggested food products which can provide the deficient nutritional components.

A third step 530 includes automatically communicating the suggested food products to the remote user. The communication can be in the form of an electronic mail message sent to the remote user. The electronic mail can be sent to an electronic mail address stored in the user diet database at the time the remote user inputs personal information. Alternatively, the communication can be in the form of storing the suggested food products in a database which is accessible by the remote user through, for example, the web page associated with the nutritional planning system.

Figure 6:
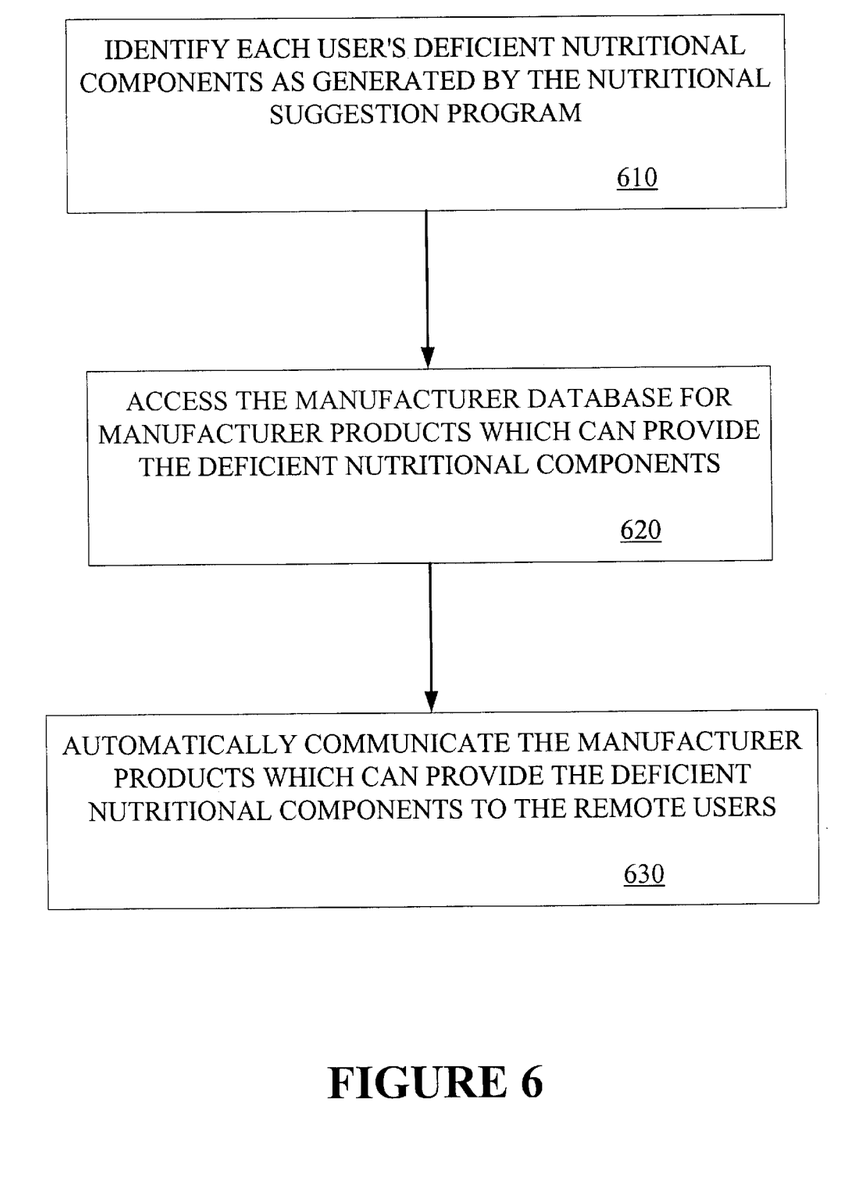
FIG. 6 is a flow chart which shows the steps included within a manufacturer suggestion program.

Another aspect of the invention includes generating a manufacturer list which includes manufacturer products within the manufacturer database which can be consumed by individual remote users to improve the dietary consumption of the remote users. The manufacturer list includes manufacturer products such as brand name nutritional snacks, brand name supplements (such as creatine), or brand name vitamins.

FIG. 6 is a flow chart which shows the steps included within a manufacturer suggestion program 240. As previously stated, the manufacturer suggestion program 240 generates a manufacturer list including manufacturer products within the manufacturer database which can be consumed by individual remote users to improve the dietary consumption of the remote users.

A first step 610 includes identifying each user's deficient nutritional components as generated by the nutritional suggestion program 220.

A second step 620 includes accessing the manufacturer database 295 for manufacturer products which can provide the deficient nutritional components.

A third step 630 includes automatically communicating the manufacturer products which can provide the deficient nutritional components to the remote users. The communication can be in the form of an electronic mail message sent to the remote user. The electronic mail can be sent to an electronic mail address stored in the user diet database at the time the remote user inputs personal information. Alternatively, the communication can be in the form of storing the manufacturer products in a database which is accessible by the remote user through, for example, the web page associated with the nutritional planning system.

Having been informed of manufacturer products which can provide the nutritional components the remote users is lacking, the remote user can make an informed decision as to which manufacturer products to purchase.

Figure 7:
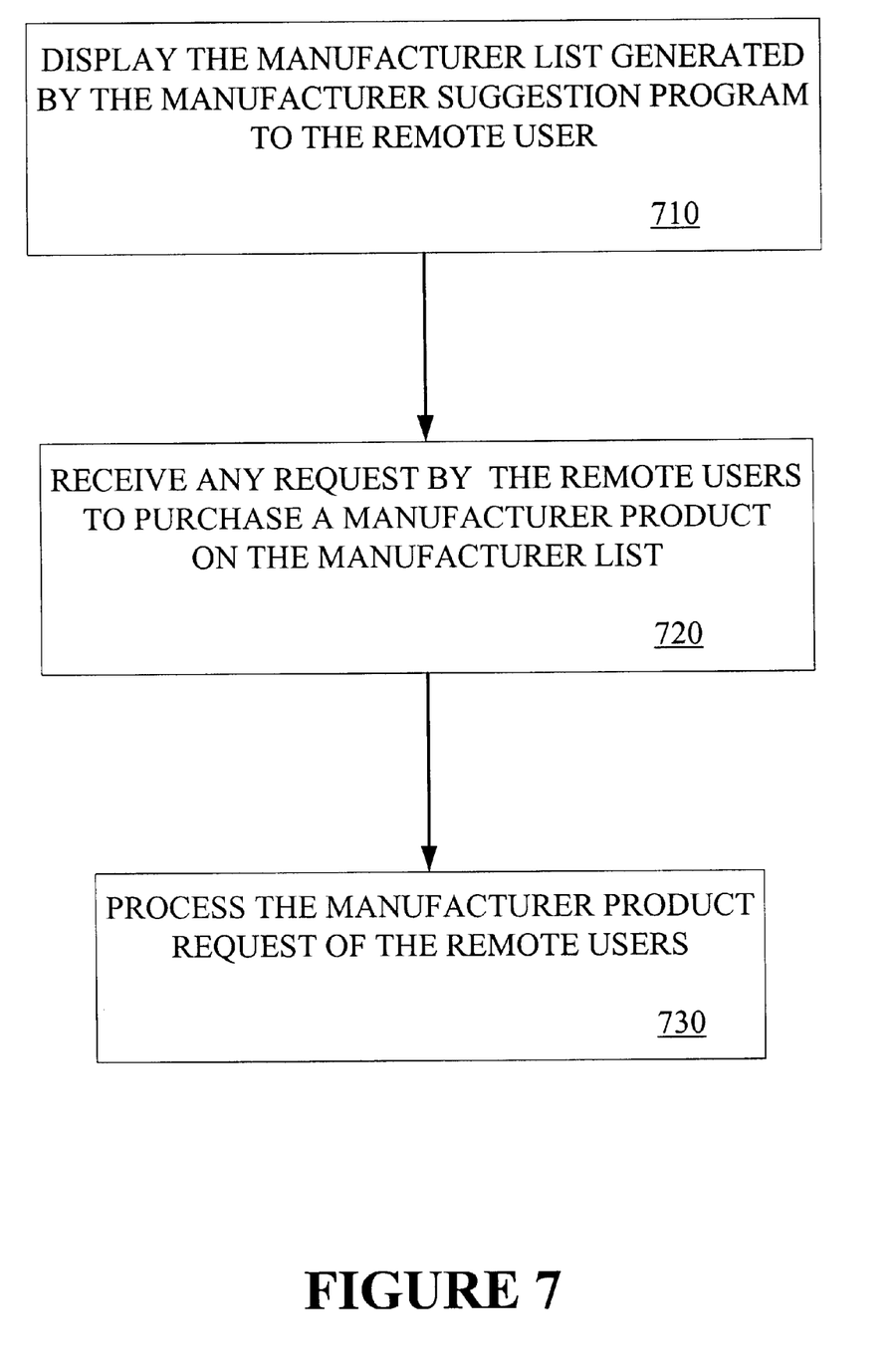
FIG. 7 is a flow chart which shows the steps included within a manufacturer transaction program.

Another aspect of the invention includes receiving money orders from remote users for manufacturer products, sending the orders to a corresponding manufacturer, and automatically sending an acknowledgment of the order to the remote user who initiated the money order.

FIG. 7 is a flow chart which shows the steps included within the product manufacturer transaction program 250.

A first step 710 includes displaying the manufacturer list generated by the manufacturer suggestion program 240 to the remote user. Similar to previously describe automatic communication with the remote users, the process of displaying the manufacturer list to the remote users can include sending individual electronic mail messages which include the manufacturer list, or displaying the manufacturer list on a web page which is controlled by the host server 100.

A second step 720 include receiving any request by the remote users to purchase a manufacturer product on the manufacturer list. The manufacturer product request are generally made over the computer network 110. If no request are made, then the product manufacturer transaction program 250 is done. If request(s) are received, then a third step 730 is executed.

The fifth step 750 includes processing the manufacturer product request of the remote users. Basically, this includes completing an order for a product. This can be accomplished by communicating the order to the manufacturer of the product through the network 110. Further, payment of the product can be completed simultaneous with the request. For example, the remote user can enter a credit card number which provides payment for the good or services requested by the remote user.

Although specific embodiments of the invention have been described and illustrated, the invention is not to be limited to the specific forms or arrangements of parts so described and illustrated. The invention is limited only by the claims.

What is claimed:

1. A nutritional planning system operational on a host server connected to a computer network, the computer network providing communication between the host server and a plurality of remote individual users, the nutritional planning system comprising:

a nutrition database in communication with the host server, the nutrition database comprising dietary components of a plurality of food types;

a user diet database in communication with the remote users and in communication with the host server, the user diet database receiving dietary information from the remote users, the dietary information comprising foods consumed by the remote users;

a recommended diet database in communication with the host server, the recommended diet database comprising recommended dietary information;

the host server comprising:
- a nutritional analysis program for determining a nutritional composition of the dietary information of the remote users by retrieving the dietary components of food types within the nutrition database which correspond with the foods consumed by the remote users;
- means for automatically communicating through the computer network to each of the remote users the nutritional composition of the dietary information of the remote user;
- a nutritional suggestion program for generating suggested modifications of the remote user's diet to improve a dietary composition of each remote user's diet based upon the dietary information of the remote user and the recommended dietary information stored within the recommended diet database; and
- means for automatically communicating the suggested modifications of the remote user's diet through the computer network to the remote users.

2. The nutritional planning system of claim 1, further comprising:
- a product suggestion database in communication with the host server, the product suggestion database comprising products which can be suggested to each remote user based upon the suggested modifications of the remote users diet;
- a product suggestion program for generating a product list comprising products within the product suggestion database which can be consumed by individual remote users to improve the dietary consumption of the remote users; and
- means for automatically communicating the product list through the computer network to the remote users.

3. The nutritional planning system of claim 2, further comprising:
- a product suggestion database in communication with the host server, the product suggestion database comprising products which can be suggested to each remote user based upon the suggested modifications of the remote users diet;
- a manufacturer database in communication with the host server, the manufacturer database comprising manufacturer products which can be suggested to each remote user based upon the suggested modifications of the remote users diet;
- a manufacturer suggestion program for generating a manufacturer list comprising manufacturer products within the manufacturer database which can be consumed by individual remote users to improve the dietary consumption of the remote users; and
- means for automatically communicating the manufacturer list through the computer network to the remote users.

4. The nutritional planning system of claim 3, further comprising:
- a manufacturer transaction program for receiving money orders from remote users for manufacturer products, sending the orders to a corresponding manufacturer, and automatically sending an acknowledgment of the order to the remote user who initiated the money order.

5. The nutritional planning system of claim 3, wherein determining the nutritional composition of the dietary information of the remote users comprises:
- means for identifying a food item within the dietary information;
- means for retrieving dietary components of the food item from the nutrition database;
- means for summing the dietary components of the food item with the corresponding dietary components of previously identified food items.

6. The nutritional planning system of claim 5, wherein generating suggested modifications of the remote user's diet comprises:
- means for accessing the recommended dietary information of the remote user based upon personal information of the remote user;
- means for determining a difference between the recommended dietary information and the summed dietary components of the dietary information;
- thereby depicting excess dietary components and deficient dietary components of the dietary information.

7. The nutritional planning system of claim 6, wherein generating a product list comprises:
- means for identifying the deficient dietary components;
- means for accessing the product suggestion database for products which can provide the deficient dietary components.

8. The nutritional planning system of claim 6, wherein generating a manufacturer list comprises:
- means for identifying the deficient dietary components;
- means for accessing the manufacturer database for manufacturer products which can provide the deficient dietary components.

9. The nutritional planning system of claim 1, wherein the means for automatically communicating through the computer network to each of the remote users the nutritional composition of the dietary information of the remote user, and the means for automatically communicating the suggested modifications of the remote user's diet through the computer network to the remote users comprises:
- sending an electronic message to each of the remote users, the electronic message comprising the nutritional composition of the dietary information and the suggested modifications of the remote user's diet.

10. The nutritional planning system of claim 1, wherein the means for automatically communicating through the computer network to each of the remote users the nutritional composition of the dietary information of the remote user, and the means for automatically communicating the suggested modifications of the remote user's diet through the computer network to the remote users comprises:
- storing the nutritional composition of the dietary information and the suggested modifications of the remote user's diet on a web page of the host server which is accessible through the computer network by the remote users.

11. A nutritional planning method operational on a host server connected to a computer network, the computer network providing communication between the host server and a plurality of remote individual users, the nutritional planning method comprising:
- receiving dietary information from the remote users, the dietary information comprising food consumed by the remote users;
- storing the dietary information in a user diet database;
- determining the nutritional composition of the remote user's dietary information by retrieving nutritional information from a nutrition database of food types corresponding to the foods consumed by the remote user; and
- automatically communicating the nutritional composition of each remote user's dietary information to the remote users;

generating suggested modifications of the remote user's diet based upon the nutritional composition of each remote user's dietary information and recommended dietary information stored within a recommended diet database; and automatically communicating the suggested modifications of each remote user's diet to the remote users.

12. The nutritional planning method of claim 11, further comprising:

generating a product list comprising products within a product suggestion database which can be consumed by individual remote users to improve the dietary consumption of the remote users; and automatically communicating the product list through the computer network to the remote users.

13. The nutritional planning method of claim 12, further comprising:

generating a manufacturer list comprising manufacturer products within a manufacturer database which can be consumed by individual remote users to improve the dietary consumption of the remote users; and automatically communicating the manufacturer list through the computer network to the remote users.

14. The nutritional planning method of claim 13, further comprising:

receiving money orders from remote users for manufacturer products, sending the orders to a corresponding manufacturer, and automatically sending an acknowledgment of the order to the remote user who initiated the money order.

* * * * *